United States Patent
Ludlum et al.

(10) Patent No.: US 11,754,539 B2
(45) Date of Patent: Sep. 12, 2023

(54) SYSTEM AND COMPUTER-IMPLEMENTED METHOD FOR EXTRAPOLATING CALIBRATION SPECTRA

(71) Applicant: SpectraSensors, Inc., Rancho Cucamonga, CA (US)

(72) Inventors: Kevin Ludlum, Freiburg (DE); Marc Winter, Gelnhausen (DE); Benjamin Scherer, Oberried (DE); Xiang Liu, Rancho Cucamonga, CA (US)

(73) Assignee: Endress+Hauser Optical Analysis, Inc., Ann Arbor, MI (US)

( * ) Notice: Subject to any disclaimer, the term of this patent is extended or adjusted under 35 U.S.C. 154(b) by 306 days.

(21) Appl. No.: 16/842,849

(22) Filed: Apr. 8, 2020

(65) Prior Publication Data

US 2021/0318280 A1 Oct. 14, 2021

(51) Int. Cl.
*G06N 3/08* (2023.01)
*G01N 33/00* (2006.01)
*G06N 20/00* (2019.01)
*G01N 21/31* (2006.01)

(52) U.S. Cl.
CPC ......... *G01N 33/0006* (2013.01); *G01N 21/31* (2013.01); *G01N 33/0036* (2013.01); *G06N 3/08* (2013.01); *G06N 20/00* (2019.01)

(58) Field of Classification Search
CPC .............. G01N 33/0006; G01N 21/31; G01N 33/0036; G01N 21/3504; G01N 21/359; G01N 2021/399; G01N 2201/129; G01N 21/274; G01N 21/39; G06N 3/08; G06N 20/00; G06F 30/27; G06F 2119/02
See application file for complete search history.

(56) References Cited

U.S. PATENT DOCUMENTS

2012/0136483 A1\* 5/2012 Haffner .................. G01N 21/39
                                                   700/274
2020/0371076 A1\* 11/2020 Koenig .............. G01N 33/0031

FOREIGN PATENT DOCUMENTS

CN          104614337 A  \*  5/2015
EP          2458351 A1       5/2012
WO          2013089764 A1    6/2013

OTHER PUBLICATIONS

Translation of CN 104614337 A (Year: 2015).\*

\* cited by examiner

*Primary Examiner* — David P Porta
*Assistant Examiner* — Mamadou Faye
(74) *Attorney, Agent, or Firm* — Kelly J. Smith; Endress+Hauser (USA) Holding, Inc.

(57) ABSTRACT

The present disclosure relates to a computer-implemented method for forecasting calibration spectra including a step of providing a machine learning model trained using historical calibration data corresponding to different gas species at different pressures. The computer-implemented method also includes steps of performing a calibration scan of one gas species at one pressure using an analyzer and generating calibration curves for the analyzer corresponding to one or multiple gas species at multiple pressures using the machine learning model and the calibration scan. Thereafter, a spectrum is obtained using the analyzer, and a concentration measurement is generated using the spectrum and at least one of the calibration curves.

20 Claims, 3 Drawing Sheets

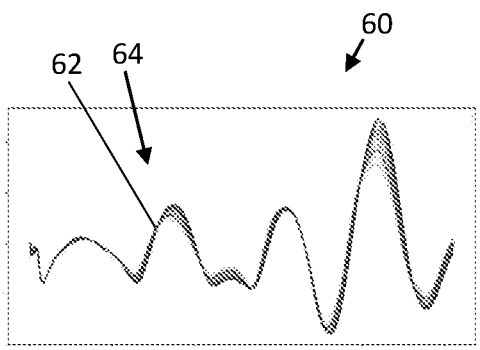
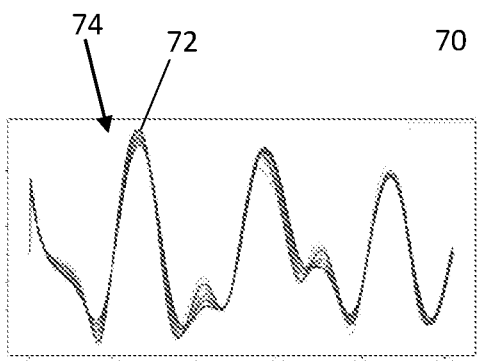
FIG. 3a　　　　　FIG. 3b
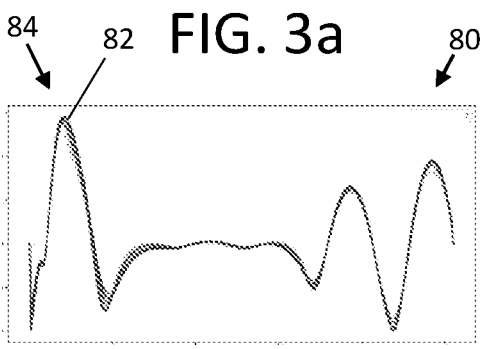
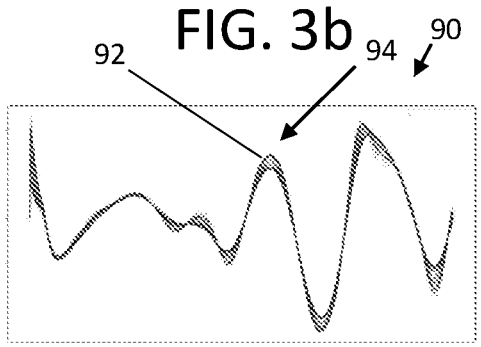
FIG. 3c　　　　　FIG. 3d
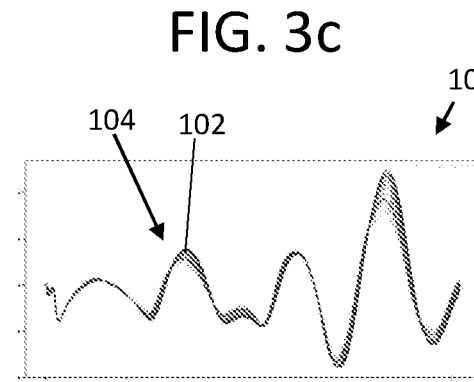
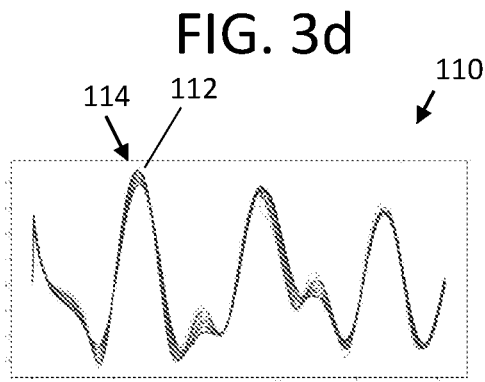
FIG. 4a　　　　　FIG. 4b
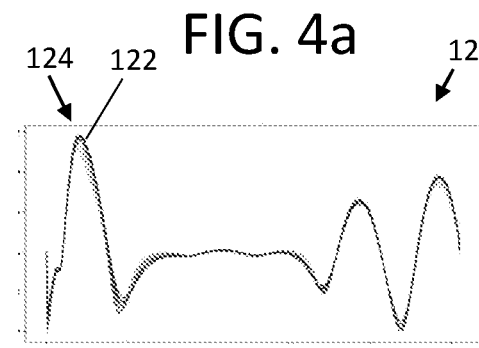
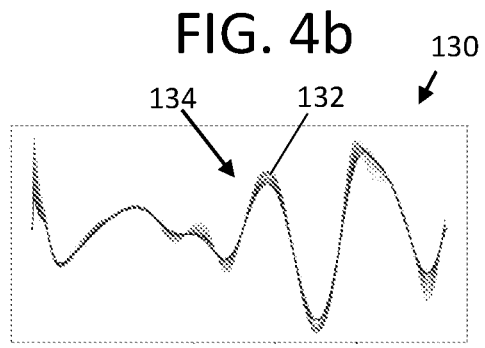
FIG. 4c　　　　　FIG. 4d

SYSTEM AND COMPUTER-IMPLEMENTED METHOD FOR EXTRAPOLATING CALIBRATION SPECTRA

TECHNICAL FIELD

The present disclosure relates to the forecasting of calibration spectra using a machine learning model.

BACKGROUND

To calibrate an analytical device, a calibration fluid of known contents and quantities is passed through the device, producing measurements of known concentration. If these measurements are not consistent with the known quantities in the calibration fluid, the analytical device is adjusted accordingly. Calibration of complex analytical devices, such as analyzers or, more specifically, process analyzers, can be time consuming and labor intensive. To make a measurement that is robust against outside effects and changes that occur over time, many factors need to be calibrated at the factory.

For example, with a TDLAS (Tunable Diode Laser Absorption Spectroscopy) analyzer, the spectra of the target analyte and the main components of the background gas matrix have to be measured at different environmental parameters, including pressure and temperature. The state-of-the-art consists of either assuming a constant device function, which allows the use of the same matrix for each instrument, or measuring all spectra required for the calibration matrix for each individual instrument. The former method using the same calibration matrix, while saving time and resources, inherently introduces uncertainty into the measurement results, due to variations from device to device. The latter method of measuring all elements of the calibration matrix, while accounting for the specific device functions does require high amounts of time and resources. Both methods are not able to account for device aging occurring in the field, among other factors.

SUMMARY

In one aspect, a computer-implemented method for forecasting calibration spectra includes a step of providing a machine learning model trained using historical calibration data corresponding to different gas species at different pressures. The computer-implemented method also includes steps of performing a calibration scan of one gas species at one pressure using an analyzer and generating calibration curves for the analyzer corresponding to one or multiple gas species at multiple pressures using the machine learning model and the calibration scan. Thereafter, a spectrum is obtained using the analyzer, and a concentration measurement is generated using the spectrum and at least one of the generated calibration curves.

In another aspect, a system includes computer hardware comprising at least one programmable processor and a machine-readable medium storing instructions that, when executed by the at least one programmable processor, cause the computer hardware to perform operations including providing a machine learning model trained using historical calibration data corresponding to different gas species at different pressures. Additional operations include performing a calibration scan of one gas species at one pressure using an analyzer, generating calibration curves for the analyzer corresponding to one or multiple gas species at multiple pressures using the machine learning model and the calibration scan, obtaining a spectrum using the analyzer, and generating a concentration measurement using the spectrum and at least one of the generated calibration curves.

In another aspect, a computer program product includes a machine-readable storage medium encoding instructions that, when executed by one or more programmable processors, cause the one or more programmable processors to perform operations including providing a machine learning model trained using historical calibration data corresponding to different gas species at different pressures. Additional operations include performing a calibration scan of one gas species at one pressure using an analyzer, generating calibration curves for the analyzer corresponding to one or multiple gas species at multiple pressures using the machine learning model and the calibration scan, obtaining a spectrum using the analyzer, and generating a concentration measurement using the spectrum and at least one of the generated calibration curves.

BRIEF DESCRIPTION OF THE DRAWINGS

In the following, the present disclosure is described in more detail with reference to the exemplary embodiments shown in the figures.

FIGS. 3a-3d show a set of graphs depicting calibration curves, including a set of calibration curves, generated by an analyzer for multiple gas species at a predetermined number of pressures;

FIGS. 4a-4d show a set of graphs depicting calibration curves, including a calibration curve generated by an analyzer for only one gas species at one predetermined pressure.

DETAILED DESCRIPTION

LAS (Light Absorption Spectroscopy) gas analyzers work on the principle of absorption of light by the gas being tested. These analyzers need only to shine a beam of light through a sample chamber, and then measure how much of specific wavelengths were absorbed by the sample. The amount of light absorbed is proportional to the concentration of the component in the fluid which absorbed light. It should be appreciated that the present disclosure is applicable to multiple analyzers, including, for example, tunable diode laser/quantum cascade laser/Interband cascade laser (TDL/QCL/ICL) gas analyzers, near infrared (NIR) or Fourier transform infrared (FTIR) spectrometers, etc.

Calibration refers to the act of adjusting the accuracy of the measurement instrument, such as an analyzer, and minimizing any measurement uncertainty. To calibrate an analyzer, for example, calibration fluid of known contents and quantities is passed through the analyzer, producing measurements of component concentration. If these measurements are not consistent with the known quantities in the calibration fluid, the process analyzer is adjusted accordingly.

Calibration curves are used to determine the concentration of unknown substances based on previous measurements of samples of known concentrations. The precision and accuracy of the measurements are dependent on the calibration curves. The better the curve the better the accuracy; the worse the curve the worse the accuracy.

Figures 1A, 1B:
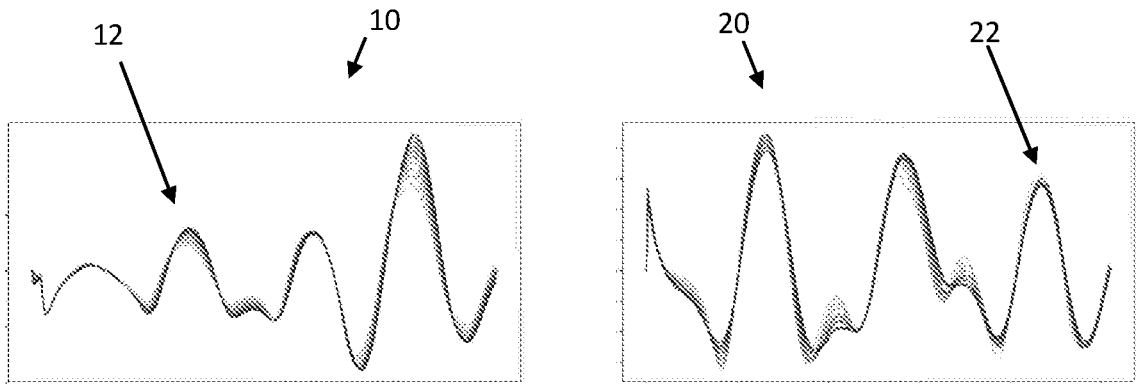
FIGS. 1a-1d show sets of graphs depicting calibration curves generated by an analyzer and indicating how instrumental response changes with pressure.

FIG. 1a shows a graph 10 including a plurality of calibration curves 12, or spectra, also referred to as reference curves, illustrating how instrumental response for each gas species changes with pressure. According to an exemplary embodiment of the present disclosure, a plurality of graphs 10, 20, 30 and 40, each containing a plurality (or set) of calibration curves 12, 22, 32 and 42, respectively, are shown. Each of the sets of the exemplary calibration curves 12, 22, 32 and 42 of each of the graphs 10, 20, 30 and 40 corresponds to one gas species at multiple pressures, as may be manually generated using an analyzer.

Figures 1C, 1D:
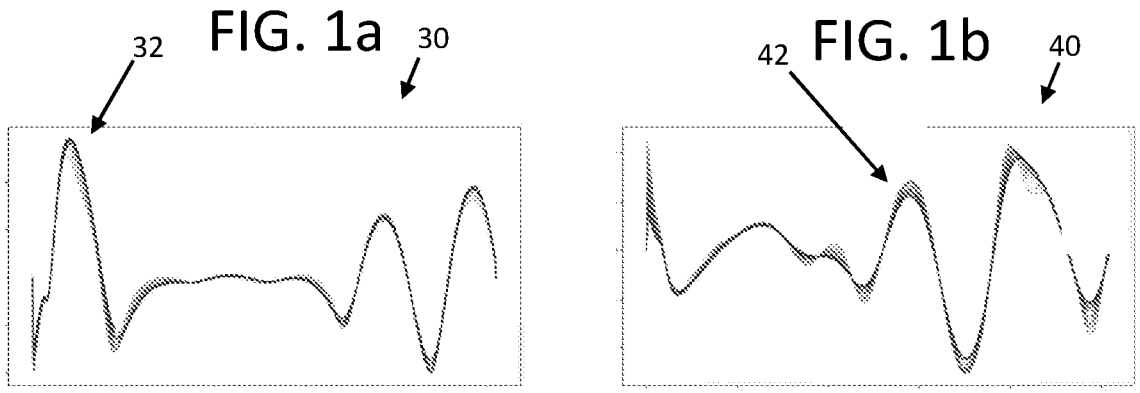

For example, each of the calibration curves 12 of FIG. 1a corresponds to methane at one of a plurality of different predetermined pressures. The calibration curves 22 of FIG. 1b each correspond to H2S at one of a plurality of different predetermined pressures, the calibration curves 32 of FIG. 1c correspond to CO2 at one of a plurality of different predetermined pressures, and the calibration curves 42 of FIG. 1d correspond to ethane at one of a plurality of different predetermined pressures.

Although four different gas species are shown in the drawings, it should be appreciated that the present disclosure may be applicable to a plurality of different gas species. For example, the present disclosure may be applicable to additional gas species such as, for example, hydrogen sulfide, acetylene, ammonia, carbon dioxide, water vapor/moisture, oxygen, hydrogen chloride, methane, carbon monoxide, methanol, ethane, ethylene, methyl acetylene, propadiene, nitrogen oxides, and sulfur oxides.

Instrument calibration is an essential stage in most measurement procedures. It involves a set of operations that establish the relationship between the output of the measurement system and the accepted values of the calibration standards. This typically involves the preparation of a set of standards containing a known amount of the analyte of interest, measuring the instrument response for each standard and establishing the relationship between the instrument response and analyte concentration. This relationship is then used to transform measurements made on test samples into estimates of the amount of analyte present.

Figure 2:
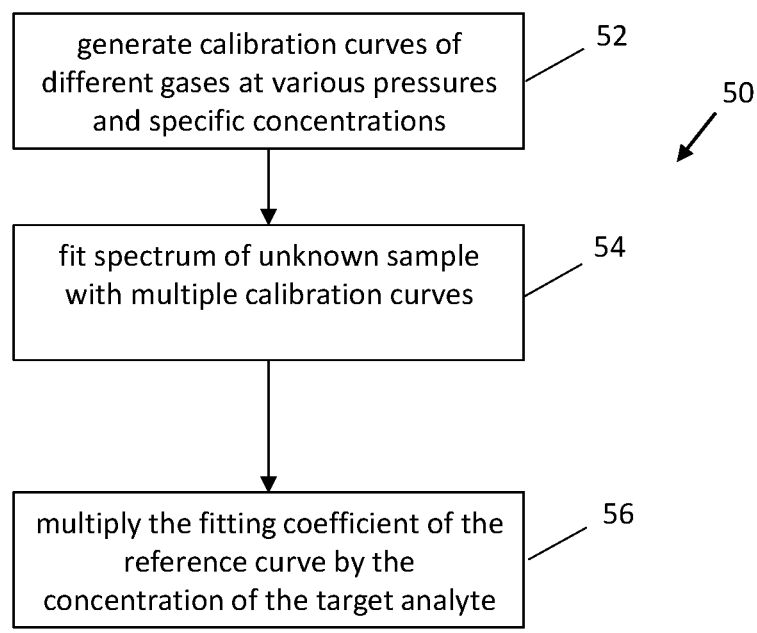
FIG. 2 shows a flow diagram of method steps for determining the concentration of a substance in an unknown sample, such as by using information from the graphs of FIGS. 1a-1d.

Turning now to FIG. 2, a partial flow diagram 50 is shown. At step one, box 52, a set of calibration curves of different gases at various pressures and specific concentrations are generated, such as manually, and saved in a data storage device of the analyzer, such as those shown in FIGS. 1a, 1b, 1c and 1d. A predetermined number of calibration curves are generated and saved during calibration for later use in real time measurements of unknown gas samples. However, a larger or smaller number of calibration curves may be generated and may incorporate the teachings of the present disclosure.

At step two, when a spectrum of an unknown gas sample is measured, this spectrum will be fit with the multiple calibration curves. Each of these used calibration curves represent the spectral response of the analyzer for one gas species at the specific pressure of the unknown gas sample. At step three, the fitting coefficient of the reference curve representing the target analyte is multiplied by the concentration of the target analyte known during the calibration to generate the concentration of the target analyte in the unknown measurement sample.

As discussed above, a calibration curve is generated for a plurality of different pressures for each gas species. In addition to pressure, temperature, collisional broadening and/or background signals may also be considered, among others. This results in a high number of curves being manually generated. Calibrating even a single analyzer can take a relatively long period of time. Further, each analyzer is slightly different, requiring a separate calibration. For example, the current procedure is to save reference curves of different gases at various pressures. The entire process of saving curves can take hours and might even need to be repeated if errors occur during the process. Further, the system is not always stable during the process of saving curves, and there is nothing in the system to account for errors that occur while saving curves.

Neural networks are a set of algorithms, modeled loosely after the human brain, that are designed to recognize patterns. They interpret sensory data through a kind of machine perception, labeling, or clustering raw input. The patterns they recognize are numerical, contained in vectors, into which all real-world data, be it images, sound, text, or time series, must be translated. The procedure used to carry out the learning process in a neural network is called the optimization algorithm.

According to the present disclosure, the neural network models can generate calibration/reference curves from a small set of calibration samples, learn the differences between the analyzers and create a function to map to different pressures or different gas species. According to one architecture, the neural network may be developed using the Keras API and may be a three-layer fully connected neural network. For example, layer one uses ReLu activation function and contains greater than 100 nodes, layer two uses tan h activation function and contains approximately 100 nodes, and layer three uses ReLu activation function and contains less than 100 nodes.

Neural networks and other forms of artificial intelligence are known and, thus, won't be discussed herein in greater detail. It should be appreciated that the present disclosure may utilize any of a variety of known machine learning strategies. For example, as an alternative to a neural network model, the present disclosure may use alternative machine learning models, such as, for example, a partial least squares (PLS) model, an inverse least square (ILS) model, a classic least squares (CLS) model or a principal component regression (PCR) model.

FIGS. 3a-3d show sets of graphs 60, 70, 80 and 90 depicting calibration curves 62, 72, 82 and 92, respectively, manually generated for each gas species (e.g., methane, hydrogen sulfide, carbon dioxide, and ethane) at a predetermined pressure. That is, one curve 62, 72, 82 and 92 may be generated for each gas species at one predetermined pressure, and sets of additional curves 64, 74, 84 and 94 corresponding to each gas species at the additional predetermined pressures may be generated using a machine learning model, such as, for example, a neural network model. The information from one curve to another may be highly correlated. The manually generated curves 62, 72, 82 and 92 may be used to further train the neural network model in a known fashion.

FIGS. 4a-4d show a set of graphs 100, 110, 120 and 130 depicting calibration curves 102, 112, 122 and 132 generated for each gas species at one predetermined pressure. In particular, calibration curves 102 and 112 each correspond to one gas species (e.g., methane and hydrogen sulfide) at one predetermined pressure and may be manually generated.

That is, a calibration scan of one gas species at one pressure using an analyzer may be performed.

The sets of additional calibration curves for the other gas species 122, 132 at the same one predetermined pressure, as well as for other predetermined pressures 104, 114, 124 and 134 for the plurality of predetermined calibration curves to be used for the analyzer corresponding to multiple gas species at multiple pressures may be generated using the neural network model, or an alternative machine learning model, and the resulting spectra from the calibration scan.

Figure 5:
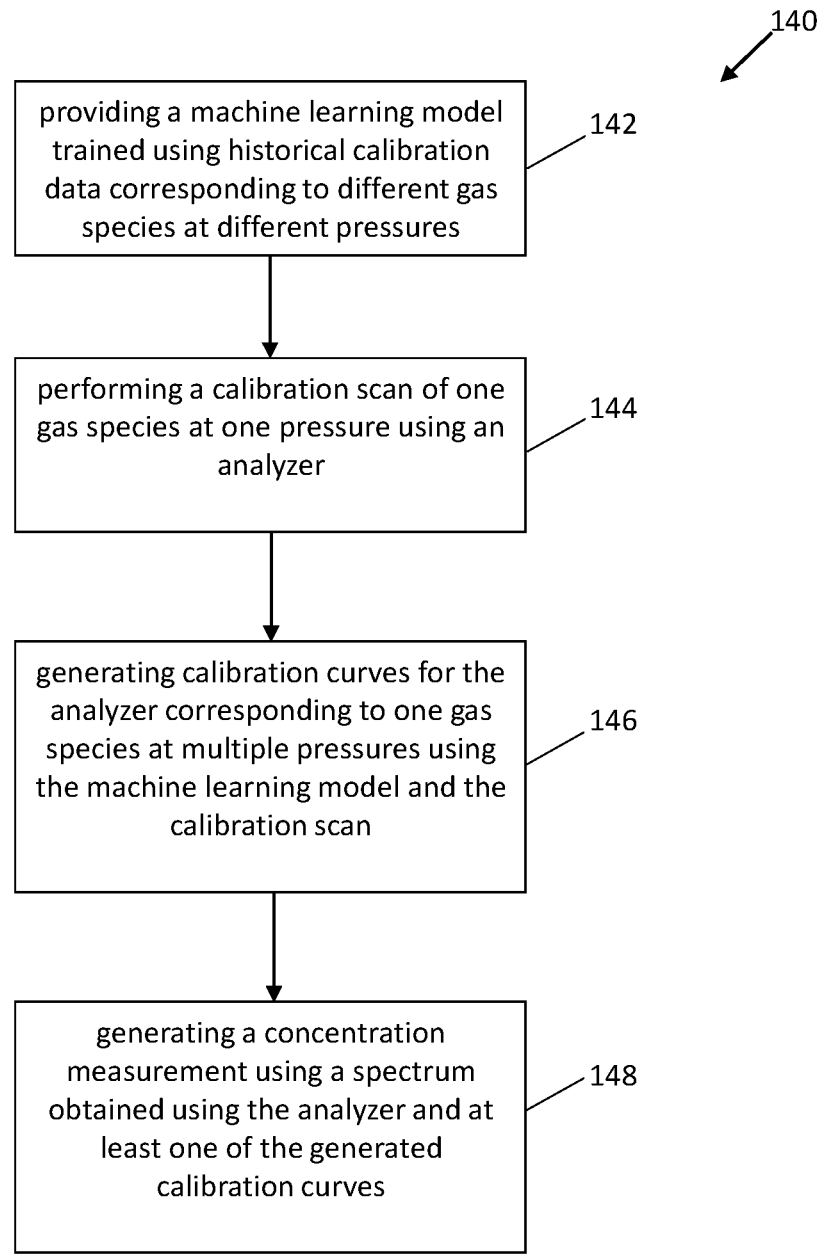
FIG. 5 shows a flow diagram of method steps for determining concentration of a substance in an unknown sample, such as by using information from the graphs of FIGS. 3a-3d and/or FIGS. 4a-4d.

With reference to the partial flow diagram 140 of FIG. 5, an exemplary method of the present disclosure is described, which may include training the neural network with historical calibration data and using the trained neural network to calibrate multiple analyzers fitting into the parameter space (e.g., gas composition and pressure of samples to be measured by the analyzer). At a first step 142, a neural network model is provided that is trained using historical calibration data corresponding to different gas species at different pressures. For example, the neural network model could use historical data gathered from the manually generated curves described above.

At another step 144 a calibration scan of one gas species at one pressure is performed using an analyzer. Alternatively, multiple calibration scans, each of which for a different gas species, all at one pressure, can be performed using an analyzer. After that 146, calibration curves for the analyzer corresponding to multiple gas species at multiple pressures can be generated using the neural network model and the calibration scan or resulting spectra. For example, a remainder of each of the sets of calibration curves shown in FIGS. 1a, 1b, 1c and 1d may be generated using the trained neural network.

At step 148, the set of generated calibration curves for a specific analyzer may be used to determine a concentration measurement using the measured spectrum of an unknown sample and a subset of the generated calibration curves.

Data has shown that Applicant's disclosed method is at least as good as other, traditional methods.

The invention claimed is:

1. A computer-implemented method for forecasting calibration spectra, comprising:
providing a machine learning model trained using historical calibration data corresponding to different gas species at different pressures;
performing a calibration scan of one gas species at one pressure using an analyzer;
generating calibration spectra for the analyzer corresponding to one or multiple gas species at multiple pressures using the machine learning model and the calibration scan;
obtaining a spectrum using the analyzer; and
generating a concentration measurement using the spectrum and at least one of the generated calibration spectra.

2. The computer-implemented method of claim 1, further including generating calibration spectra for the analyzer corresponding to multiple gas species at multiple pressures.

3. The computer-implemented method of claim 1, further including performing multiple calibration scans at one pressure, wherein each of the calibration scans corresponds to a different gas species at the one pressure using the analyzer.

4. The computer-implemented method of claim 1, wherein the one gas is hydrogen sulfide, acetylene, ammonia, carbon dioxide, or water.

5. The computer-implemented method of claim 1, wherein the one gas is oxygen, hydrogen chloride, methane, or carbon monoxide.

6. The computer-implemented method of claim 1, wherein the one gas is methanol, ethane, ethylene, methyl acetylene, propadiene, nitrogen oxides, or sulfur oxides.

7. The computer-implemented method of claim 1, wherein the machine learning model includes at least one of a neural network model, a partial least squares model, an inverse least square model, a classic least square model and a principal component regression model.

8. A system for forecasting calibration spectra, comprising:
computer hardware comprising:
at least one programmable processor; and
machine-readable medium storing instructions that, when executed by the at least one programmable processor, cause the computer hardware to perform operations comprising:
providing a machine learning model trained using historical calibration data corresponding to different gas species at different pressures;
performing a calibration scan of one gas species at one pressure using an analyzer;
generating calibration spectra for the analyzer corresponding to one or multiple gas species at multiple pressures using the machine learning model and the calibration scan;
obtaining a spectrum using the analyzer; and
generating a concentration measurement using the spectrum and at least one of the generated calibration spectra.

9. The system of claim 8, further including generating calibration spectra for the analyzer corresponding to multiple gas species at multiple pressures.

10. The system of claim 8, further including performing multiple calibration scans at one pressure, wherein each of the calibration scans corresponds to a different gas species at the one pressure using the analyzer.

11. The system of claim 8, wherein the one gas is hydrogen sulfide, acetylene, ammonia, carbon dioxide, or water.

12. The system of claim 8, wherein the one gas is oxygen, hydrochloric acid, methane, or carbon monoxide.

13. The system of claim 8, wherein the one gas is methanol, ethane, ethylene, methyl acetylene, propadiene, nitrogen oxide, or sulfur oxide.

14. The system of claim 8, further including providing a neural network model trained using historical calibration data corresponding to different gas species at different pressures and temperatures.

15. The system of claim 8, wherein the machine learning model includes at least one of a neural network model, a partial least squares model, an inverse least square model, a classic least square model and a principal component regression model.

16. A computer program product comprising a machine-readable storage medium encoding instructions that, when executed by one or more programmable processors, cause the one or more programmable processors to perform operations comprising:
providing a machine learning model trained using historical calibration data corresponding to different gas species at different pressures;
performing a calibration scan of one gas species at one pressure using an analyzer;

generating calibration spectra for the analyzer corresponding to one or multiple gas species at multiple pressures using the machine learning model and the calibration scan;

obtaining a spectrum using the analyzer; and generating a concentration measurement using the spectrum and at least one of the generated calibration spectra.

17. The computer program product of claim 16, further including generating calibration spectra for the analyzer corresponding to multiple gas species at multiple pressures.

18. The computer program product of claim 16, further including performing multiple calibration scans at one pressure, wherein each of the calibration scans corresponds to a different gas species at the one pressure using the analyzer.

19. The computer program product of claim 16, further including providing a neural network model trained using historical calibration data corresponding to different gas species at different pressures and temperatures.

20. The computer program product of claim 16, wherein the machine learning model includes at least one of a neural network model, a partial least squares model, an inverse least squares model, a classic least squares model and a principal component regression model.

* * * * *